US012599535B2

(12) United States Patent
  Poon

(10) Patent No.: US 12,599,535 B2
(45) Date of Patent: Apr. 14, 2026

(54) EXTERNAL COUNTERPULSATION SYSTEM

(71) Applicant: Michael Poon, New York, NY (US)

(72) Inventor: Michael Poon, New York, NY (US)

(73) Assignee: Michael Poon, New York, NY (US)

( * ) Notice: Subject to any disclaimer, the term of this patent is extended or adjusted under 35 U.S.C. 154(b) by 390 days.

(21) Appl. No.: 16/884,402

(22) Filed: May 27, 2020

(65) Prior Publication Data

US 2020/0297574 A1     Sep. 24, 2020

Related U.S. Application Data

(63) Continuation of application No. PCT/US2019/012663, filed on Jan. 8, 2019.
(Continued)

(51) Int. Cl.
  *A61H 9/00* (2006.01)
  *A61H 31/00* (2006.01)
  (Continued)

(52) U.S. Cl.
  CPC ......... *A61H 9/0092* (2013.01); *A61H 31/005* (2013.01); *A61H 31/006* (2013.01);
  (Continued)

(58) Field of Classification Search
  CPC .......... A61M 2230/06; A61M 2021/00; A61M 2021/0022; A61M 21/00; A61H 2230/06;
  (Continued)

(56) References Cited

U.S. PATENT DOCUMENTS

| | | | |
|---|---|---|---|
| 3,215,938 A | 11/1965 | Spencer et al. | |
| 3,527,207 A | 9/1970 | Gottfried | |

(Continued)

FOREIGN PATENT DOCUMENTS

| | | |
|---|---|---|
| CN | 2425646 Y | 4/2001 |
| CN | 200966713 Y | 10/2007 |

(Continued)

OTHER PUBLICATIONS

"Evidence lacking for 'inflatable-pants' heart failure therapy," http://www.eurekalert.org/pub_releases/2006-02/cfta-elf022106.php, dated Feb. 21, 2006.

(Continued)

*Primary Examiner* — Timothy A Musselman
(74) *Attorney, Agent, or Firm* — Goodwin Procter LLP

(57) ABSTRACT

Improved systems and methods for performing external counterpulsation (ECP) treatment are described. The system can be more compact and portable than conventional devices and, in some cases, can be incorporated into a pair of pants or a jumpsuit, such that the user can remain ambulatory during treatment. In various instances, the ECP techniques can include applying complex pulse sequences and treating conditions including cognitive disorders, diabetes, and renal disease, among others. The various techniques can also be used in emergency cardiac situations. The techniques can also be used to provide users with the benefits of exercise, without needing to experience the strain and difficulty associated with conventional cardiovascular exercise routines.

14 Claims, 7 Drawing Sheets

Related U.S. Application Data

(60) Provisional application No. 62/614,553, filed on Jan. 8, 2018.

(51) Int. Cl.
| | |
|---|---|
| *A61M 21/00* | (2006.01) |
| *A61H 11/00* | (2006.01) |

(52) U.S. Cl.
CPC ....... *A61M 21/00* (2013.01); *A61H 2011/005* (2013.01); *A61H 2201/163* (2013.01); *A61H 2201/1638* (2013.01); *A61H 2201/1642* (2013.01); *A61H 2201/1645* (2013.01); *A61H 2201/165* (2013.01); *A61H 2205/06* (2013.01); *A61H 2205/086* (2013.01); *A61H 2205/088* (2013.01); *A61H 2205/108* (2013.01); *A61H 2209/00* (2013.01); *A61H 2230/065* (2013.01); *A61M 2021/0022* (2013.01); *A61M 2230/06* (2013.01)

(58) Field of Classification Search
CPC .......... A61H 2230/065; A61H 2209/00; A61H 2205/06; A61H 2205/086; A61H 2201/163; A61H 2201/1638; A61H 2201/1642; A61H 2201/1645; A61H 2201/165; A61H 2011/00; A61H 2011/005; A61H 31/005; A61H 31/006; A61H 9/0092
See application file for complete search history.

(56) References Cited

U.S. PATENT DOCUMENTS

| | | | |
|---|---|---|---|
| 3,866,604 | A | 2/1975 | Curless et al. |
| 4,370,975 | A | 2/1983 | Wright |
| 4,396,010 | A | 8/1983 | Arkans |
| 4,613,765 | A | 9/1986 | Honig |
| 4,753,226 | A | 6/1988 | Zheng et al. |
| 5,031,604 | A | 7/1991 | Dye |
| 5,437,610 | A | 8/1995 | Cariapa et al. |
| 5,871,526 | A | 2/1999 | Gibbs et al. |
| 5,968,073 | A | 10/1999 | Jacobs |
| 5,997,540 | A | 12/1999 | Zheng et al. |
| 6,450,942 | B1 | 9/2002 | Lapanashvili et al. |
| 6,450,981 | B1 | 9/2002 | Shabty et al. |
| 6,589,267 | B1 | 7/2003 | Hui |
| 6,832,982 | B1 | 12/2004 | Lapanashvili et al. |
| 7,048,702 | B2 | 5/2006 | Hui |
| 7,314,478 | B2 | 1/2008 | Hui |
| 7,491,185 | B2 | 2/2009 | Couvillon, Jr. |
| 8,043,239 | B2 | 10/2011 | Rastegar et al. |
| 8,579,792 | B2 | 11/2013 | Pickett et al. |
| 8,801,643 | B2 | 8/2014 | Deshpande et al. |
| 9,265,693 | B2 | 2/2016 | Sudarev et al. |
| 2003/0032904 | A1 | 2/2003 | Egger |
| 2003/0216651 | A1 | 11/2003 | Burns et al. |
| 2003/0233061 | A1 | 12/2003 | Hui |
| 2005/0177078 | A1 | 8/2005 | Loeb et al. |
| 2005/0240087 | A1* | 10/2005 | Keenan ................ A61B 5/6804 600/509 |
| 2006/0058715 | A1 | 3/2006 | Hui et al. |
| 2006/0058716 | A1 | 3/2006 | Hui et al. |
| 2006/0058717 | A1 | 3/2006 | Hui et al. |
| 2006/0135889 | A1 | 6/2006 | Egli |
| 2007/0173886 | A1 | 7/2007 | Rousso et al. |
| 2007/0272250 | A1 | 11/2007 | Lewis |
| 2008/0033228 | A1 | 2/2008 | Rastegar et al. |
| 2009/0036938 | A1 | 2/2009 | Shipley et al. |
| 2009/0198308 | A1 | 8/2009 | Gross et al. |
| 2012/0165711 | A1 | 6/2012 | Pickett et al. |
| 2013/0102939 | A1 | 4/2013 | Sudarev |
| 2014/0221784 | A1 | 8/2014 | Pacione et al. |
| 2015/0289808 | A1 | 10/2015 | Pacione et al. |

FOREIGN PATENT DOCUMENTS

| | | |
|---|---|---|
| CN | 202409849 U | 9/2012 |
| WO | WO-2005074376 A3 | 6/2006 |
| WO | WO-2013028581 A1 | 2/2013 |
| WO | WO-14135636 A1 | 9/2014 |

OTHER PUBLICATIONS

"EECP® Therapy Patient," http://www.eecp.com/patient-setup.php (2017).
International Search Report and Written Opionion, Issued in PCT/US2019/012663, dated May 24, 2019.

* cited by examiner

700

136

130

134b

120

134b

132a

132b

EXTERNAL COUNTERPULSATION SYSTEM

CROSS-REFERENCE TO RELATED APPLICATION

This application is a continuation of and claims priority to International Patent Application No. PCT/US2019/012663, titled External Counterpulsation System, filed on Jan. 8, 2019, which claims priority to and the benefit of U.S. Provisional Patent Application No. 62/614,553, filed Jan. 8, 2018; the entire contents of both of which are incorporated herein by reference.

TECHNICAL FIELD

The invention relates generally to systems and methods for performing external counterpulsation (ECP) therapy and, more particularly, to ECP techniques featuring complex pulse sequences and used for the treatment of blood flow, cardiovascular, and metabolic disorders, as well as for cognitive conditions and in emergency situations.

BACKGROUND

Cardiovascular disease is an extremely common condition afflicting hundreds of millions of patients worldwide. According to the American Heart Association, it is the leading global cause of death. In the 1960s, it was discovered that one way to help improve the function of the heart is to augment pressure in the blood vessels during the diastole stage of the cardiac cycle (i.e., when the heart is relaxed and blood flows into the heart) and to unload the blood vessels during the systole stage of the cardiac cycle (i.e., when the heart contracts and pumps blood out of the heart).

An arterial counter-pulsator was an early device that functioned similar to a bicycle pump. This invasive device received blood during cardiac ejection through a catheter introduced into the root of the aorta through the femoral artery and pushed the blood back into circulation during diastole. In a later device, a balloon was placed at the tip of the catheter. The balloon was inflated with helium gas during diastole to generate diastolic augmentation and deflated during systole to reduce afterload. This technique became known as Intra-aortic Balloon Pumping (IABP). While IABP represented an advancement, this technique has several drawbacks. For example, it is an invasive technique requiring a surgical procedure for placement of the catheter and there is a high risk of infection.

More recently, IABP has been replaced with a non-invasive technique in which the lower extremities are wrapped with cuffs that apply an external pressure during the diastole stage and release the pressure during the systole stage. This general technique has come to be known as external counterpulsation (ECP).

Most current ECP systems use three sets of inflatable pressure cuffs wrapped around the calves, lower thighs, and upper thighs (including the buttocks). During the diastole stage, the pressure cuffs are rapidly and sequentially inflated, starting from the calves and proceeding upward to the buttocks, forcing blood flow towards and into the heart. During the systole stage, all three cuffs simultaneously deflate. FIG. 1 is a schematic diagram illustrating this pressure pulse sequence. Inflation and deflation of the cuffs can be synchronized with the cardiac cycle by a micropro-cessor to actuate inflation and deflation in response to a signal from a heart rate monitor.

To date, ECP therapy has been used primarily for the treatment of refractory angina, which is one of the few treatments for which it is cleared by the U.S. Food and Drug Administration and that is reimbursable under the Medicare and Medicaid programs. An industry leader in ECP treatment is Vasomedical, Inc. of Westbury, N.Y., that markets an ECP treatment program referred to as Enhanced External Counterpulsation (EECP®). EECP® therapy is an outpatient procedure typically administered for one to two hours per session, three to five days a week, for a total of seven to about 11 weeks or 35 sessions. During treatment, patients are required to lie in a bed with inflatable cuffs attached to their calves, thighs, and buttocks and an electrocardiogram placed on their chest to monitor their heartbeat. The system monitors the heartbeat and generally causes each inflatable cuff to apply a single pressure pulse to the patient per heartbeat. FIG. 2 is a schematic representation of a patient undergoing conventional ECP therapy constrained to a recumbent portion and attached to a large, cumbersome system.

Although conventional ECP treatment offers some demonstrated benefits, there are numerous limitations that prevent more widespread use. As a few examples, patients are confined to a bed during treatment, which is often inconvenient, the inflatable cuffs can be difficult to put on without assistance, and the inflation pump technology is outdated. In addition, ECP treatment has only been explored for treating a very small number of medical conditions.

SUMMARY

Accordingly, the present disclosure describes improved ECP treatment systems and methods. In some embodiments, the ECP treatment techniques permit a patient to be ambulatory during treatment. In various embodiments, the ECP treatment techniques can be used to treat effectively different medical conditions than refractory angina.

In various aspects, this disclosure describes improved systems and methods for performing ECP treatment. In some embodiments, the ECP treatment device is more compact and portable than conventional devices. For example, the device can be incorporated into a pair of pants or a jumpsuit, that is easily applied and removed and that permits the user to be ambulatory during treatment. In some embodiments, a control system associated with the device is programmed to actuate complex pulse sequences beyond the single pulse per heart beat sequence used in conventional techniques. As one example, multiple pulses per heart beat can be applied, as a function of heart rate and system response time.

The inventor has also discovered that ECP treatment can be used effectively to treat a wide array of conditions beyond just refractory angina. For example, the techniques described herein can be used to treat myriad conditions, such as diabetes and renal disease, and also to improve cognitive function. Further, while it may have been suggested to use ECP treatment as preventative care to prevent myocardial infarction (commonly referred to as a heart attack) and post-trauma care following a heart attack, the inventor has discovered that ECP treatment can be used in emergency situations, such as during a heart attack and when a patient is undergoing cardiac resuscitation.

In addition, the techniques described herein can provide users with the cardiovascular benefits of exercise, without the need for users to strain their bodies and impact their joints, as required by conventional cardiovascular exercise routines, such as running. This benefit can be highly advantageous for patients who are too sick to perform conventional cardiovascular exercise and for individuals who desire the effects of a cardiovascular workout without the negative side effects or difficulty of standard exercise routines. In some instances, for example, when the treatment device takes the form of pants or a jumpsuit, the ECP treatment can be worn and actuated simultaneously in conjunction with a conventional exercise routine (e.g., an upper extremity exercise routine) to provide an enhanced benefit.

In one aspect, the invention relates to a counterpulsation system. The counterpulsation system can include a monitor adapted to sense a heartbeat of a user, a pulsation unit adapted to apply pressure pulses to at least a lower body of the user, and a controller adapted to receive sensed heartbeats from the monitor and to control the pulsation unit to apply at least two pressure pulses between successive heartbeats of the user.

In some embodiments of the above aspect, the pulsation unit is externally disposed about at least one of a buttock region, a thigh region, a hip region, and a leg region of the user and may include at least one inflatable sleeve for the upper extremities. In some embodiments, the monitor is further adapted to sense a heart rate of the user and the controller is adapted to control the pulsation unit to (i) apply three pulses between successive heartbeats when the heart rate of the user is in a range from 30 bpm to 50 bpm and (ii) apply two pulses between successive heartbeats when the heart rate of the user is in a range from 50 bpm to 80 bpm. In some cases, the monitor and/or the pulsation unit communicate wirelessly with the controller. In instances, the counterpulsation system permits the user to be ambulatory and may include a wearable garment. The counterpulsation system may be adapted to perform a therapy treatment, perform in combination with cardiac resuscitation on the user, and/or treat a cognitive impairment of the user.

In another aspect, the invention relates to a method for applying counterpulsation to a user. The method may include the steps of sensing the heartbeats of the user and applying at least two pressure pulses to a lower body of the user between successive heartbeats of the user.

In some embodiments of this aspect, the applying step is performed by a pulsation unit externally disposed about at least one of a buttock region, a thigh region, a hip region, and a leg region of the user. The method may further include the step of sensing a heart rate of the user, where the applying step includes applying (i) three pulses between successive heartbeats when the heart rate of the user is in a range from 30 bpm to 50 bpm and (ii) two pulses between successive heartbeats when the heart rate of the user is in a range from 50 bpm to 80 bpm. In some instances, both the measuring and applying steps occur while the user is ambulatory. The method may further include the step of first determining that the user requires cardiac resuscitation or first determining that the user has a cognitive impairment.

In another aspect, the invention relates to a counterpulsation system adapted for use on an individual undergoing manual or automated (e.g., mechanical) cardiopulmonary resuscitation. The system can include a monitor adapted to sense chest compression of the individual (e.g., given by a human first responder or an automated mechanical chest compression system), a pulsation unit adapted to apply counter pulsation pressure pulses to a lower body of the individual, and a controller adapted to receive sensed chest compressions from the monitor and to control the pulsation unit to apply at least one pressure pulse between successive chest compressions of the individual. In some embodiments of the above aspect, the pulsation unit may be further adapted to apply pressure pulses to an upper body (e.g., the upper extremities) of the individual.

In another aspect, the invention may relate to another method for applying counterpulsations to an individual. The method may include the steps of sensing chest compressions of the individual and applying at least one pressure pulse between successive chest compressions of the individual. In some embodiments of the above aspect, the at least one pressure pulse is applied to an upper body of the individual.

In another aspect, the invention may relate to another counterpulsation system. The counterpulsation system can include a monitor adapted to sense an irregular heartbeat of a user, a pulsation unit adapted to apply pressure pulses to a body portion of the user, and a controller adapted to receive sensed irregular heartbeats from the monitor and to control the pulsation unit to apply a variable pulse sequence as a function of the irregular heartbeat. In some embodiments of the above aspect, the variable pulse sequence may include a suspension of pulses during a first portion of a treatment period and multiple pressure pulses between successive heartbeats during a second portion of the treatment period or vice versa depending on the rhythm regularity of the user.

In another aspect, the invention may relate to another method for applying counterpulsations to a user. The method may include the steps of sensing an irregular heartbeat of the user and applying a variable pulse sequence as a function of the irregular heartbeat. In some embodiments of the above aspect, the applying step includes suspending pulses during a first portion of a treatment period and applying multiple pulses between successive heartbeats during a second portion of the treatment period.

BRIEF DESCRIPTION OF THE FIGURES

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Figure 1:
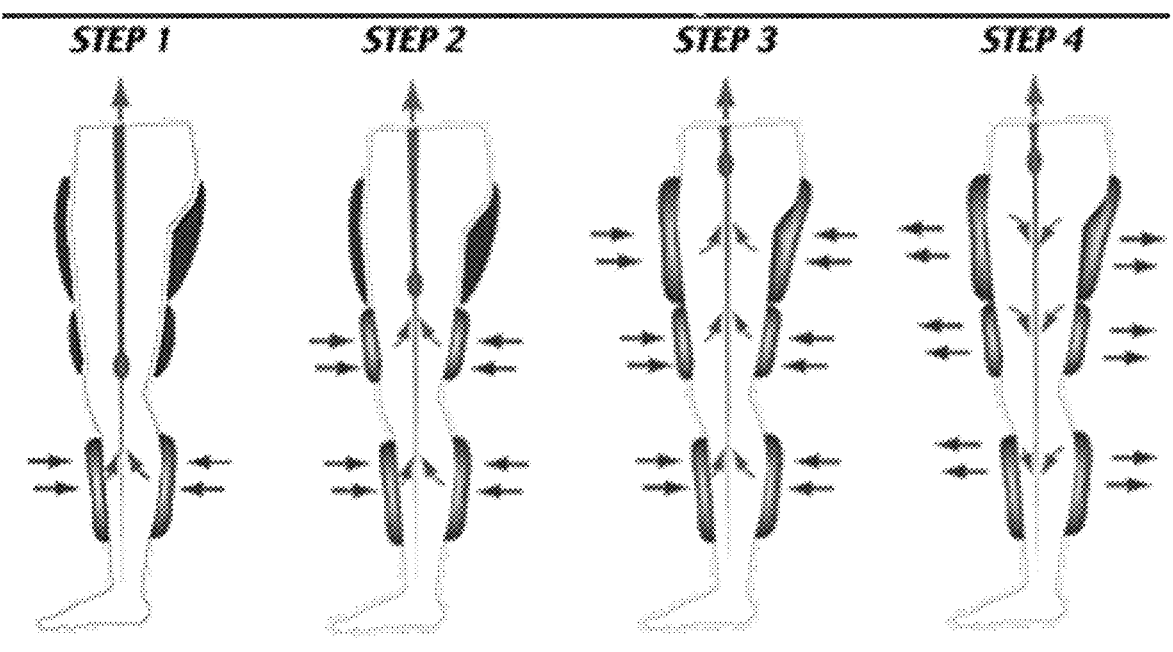
FIG. 1 is schematic diagram illustrating a prior art pressure pulse sequence applied to the legs of a user by a conventional ECP device.
Figure 2:
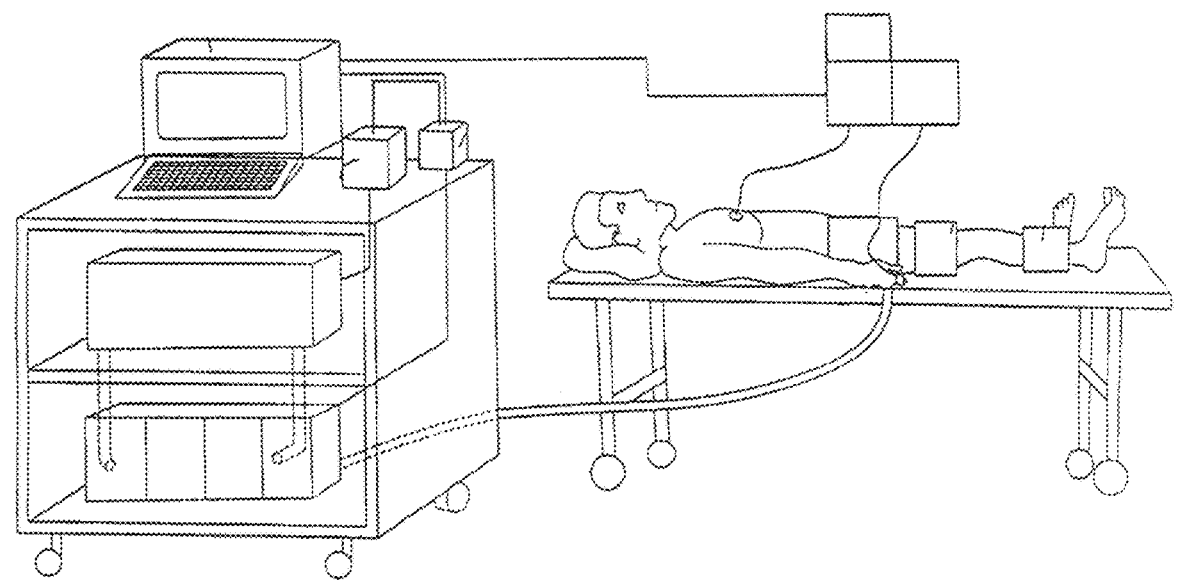
FIG. 2 is an illustration depicting a user constrained to a conventional prior art ECP system.

Embodiments of the present invention relate to an ECP treatment device that is more compact and portable than conventional devices and that includes enhanced functionality. In some instances, as shown for example in FIG. 3, the treatment device 100 can take the form of a pair of pants worn by a user 102. In other embodiments, the pants can take the form of another type of wearable garment, e.g., a jumpsuit, leggings, etc. By incorporating the treatment device into a wearable garment, the user 102 can be more ambulatory during treatment. In some embodiments, the garment can include relatively tight fitting, resilient materials, such as spandex, that can expand upon the expansion of inflatable cuffs (described below) and also relax to allow natural blood flow to occur. In some instances, the wearable garment may include an outer shell, e.g., formed from a plastic or other material having enough tensile strength resist elastic deformation upon expansion of an inflatable cuff. An outer shell with these properties may reduce the air pressure required to inflate (or deflate) the inflatable cuff within the shell (e.g., because the shell itself can provide some of the pressure necessary for inflation/deflation and/or constrain the direction in which the cuff inflates). This can reduce the size of the motor or compressor required to generate the air pressure, in some case significantly.

Although this disclosure will often describe the treatment device 100 as a wearable garment, in various embodiments, it can take many other forms as well. In general, the treatment device 100 can take any form, as long as the device 100 can perform at least one of the improved treatment techniques described herein. As one example, the treatment device 100 can take the form of a portable kit including separate inflatable cuffs (e.g., not incorporated into a garment) that can be used in a patient's home or in an ambulance. As another example, the treatment device 100 can take the form of a traditional bed having affixed cuffs, but having the functionality to perform the improved treatment techniques described herein.

As shown, the treatment device 100 can include at least three inflatable cuffs, typically three pairs of cuffs, located at various locations along the user's legs. For example, inflatable cuffs 106a, 106b can be disposed about the user's calf region, inflatable cuffs 108a, 108b can be disposed about the user's lower thigh region, and inflatable cuffs 110a, 110b can be disposed about the user's upper thigh/buttocks region. In some cases, certain cuffs (e.g., 110a, 110b) are combined into a single cuff. Although this disclosure will often describe an embodiment having three sets of inflatable cuffs, in various embodiments, the treatment device 100 can include fewer cuffs (e.g., 1 or 2 cuffs) or more cuffs (e.g., 4, 5, or 6 cuffs) and apply similar principles to those described herein. Multiple cuffs can also be provided at each location, for example, medial and lateral thigh cuffs.

In general, the inflatable cuffs can be any structure capable of controllably (i) applying an external pressure to limbs to compress blood vessels and urge blood towards the heart and (ii) releasing pressure to facilitate unrestricted delivery of blood from the heart back into the blood vessels. The inflatable cuffs can also be configured such that they are easier to put on than conventional cuffs. For example, in some cases, the inflatable cuffs can be pneumatic bladders that expand upon being filled with pressurized gas. The bladders can, for example, be incorporated within the fabric of a wearable garment. In some instances the cuffs can be covered by a hard outer casing (e.g., relative to the cuffs) that enables the cuffs to be inflated/deflated with less pressure supplied from a compressor or other source, which can reduce the size of the motor required to generate the inflation/deflation pressure which can make the system more portable.

Although this disclosure will primarily describe cuffs adapted to be filled with pressurized gas, other types of cuffs are contemplated. For example, in some cases, the cuffs can be bladders filled with liquids, gels or other materials that respond to various known stimuli (e.g., electrical, chemical, etc.) to cause the bladder to apply pressure. In still other cases, the cuffs can apply pressure by contracting upon application of a stimuli (e.g., the cuffs can include magnets that are drawn to one another upon generation of a magnetic field or employ a solenoid actuated electro-mechanical compression mechanism). Many other types of cuffs are possible and contemplated.

Figure 3:
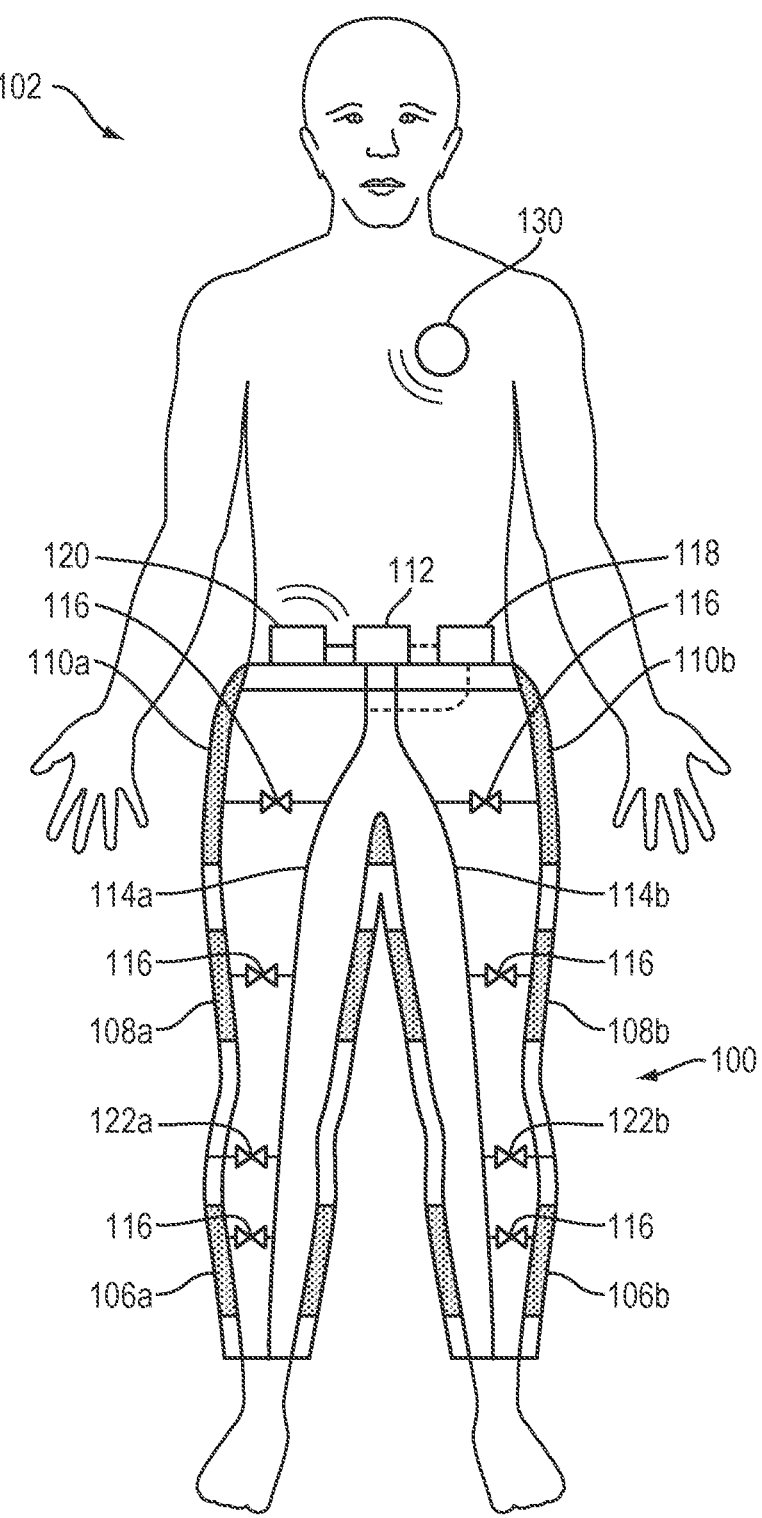
FIG. 3 is a schematic illustration of an ECP treatment device in the form of a wearable garment, according to various embodiments.

In various embodiments, the treatment device 100 includes a pressurized gas source, such as a compressor 112, that operates to produce pressurized gas used to inflate the inflatable cuffs. The pressurized gas can be delivered to the inflatable cuffs via a manifold with associated tubing and a valve network. In general, the gas distribution system can be any known structure for the controlled transport of pressurized gas. Similarly, the manifold tubing and valve network can be arranged in any way that will effectively deliver pressurized gas to multiple sets of inflatable cuffs. For example, as shown in FIG. 3, the compressor 112 can deliver pressurized gas to trunk lines or manifolds 114a, 114b, each of which is dedicated to a respective leg of the user 102. From the manifolds 114a, 114b, the gas can be selectively delivered to any of the inflatable cuffs by the opening and closing of particular valves 116, to enable selective inflation of the cuffs alone or in pairs. As shown, each inflatable cuff can have a dedicated valve 116 that connects the cuff to a manifold 114a, 114b. In general, the valves 116 can be any suitable type of valve, e.g., solenoid valves. In other embodiments, the compressor 112 can selectively deliver pressurized gas into separate dedicated gas lines for each inflatable cuff. In some embodiments, the compressor 112 delivers pressurized gas to a storage tank 118 that stores pressurized gas before being delivered to the manifolds 114a, 114b, for example to provide pneumatic capacitance to the system and attenuate compressor output pressure pulses. This can allow more pressurized gas to be available on demand to support periods of greater system operational need, without requiring the system to wait for pressure replenishment delays by the compressor 112.

In some embodiments, the inflatable cuffs can also be selectively deflated. In general, this can be accomplished using any of a variety of techniques. For example, in some embodiments, the supply of pressurized gas to the manifolds 114a, 114b can be halted and the manifolds 114a, 114b depressurized by opening bleed valves 122a, 122b that vent to ambient. Once the manifolds 114a, 114b are depressurized, the inflatable cuffs can be selectively deflated by selectively re-opening valves 116. Alternatively, all the valves can be opened simultaneously, for rapid depressurization, or in any sequence to tailor the depressurization profile.

Figure 4:
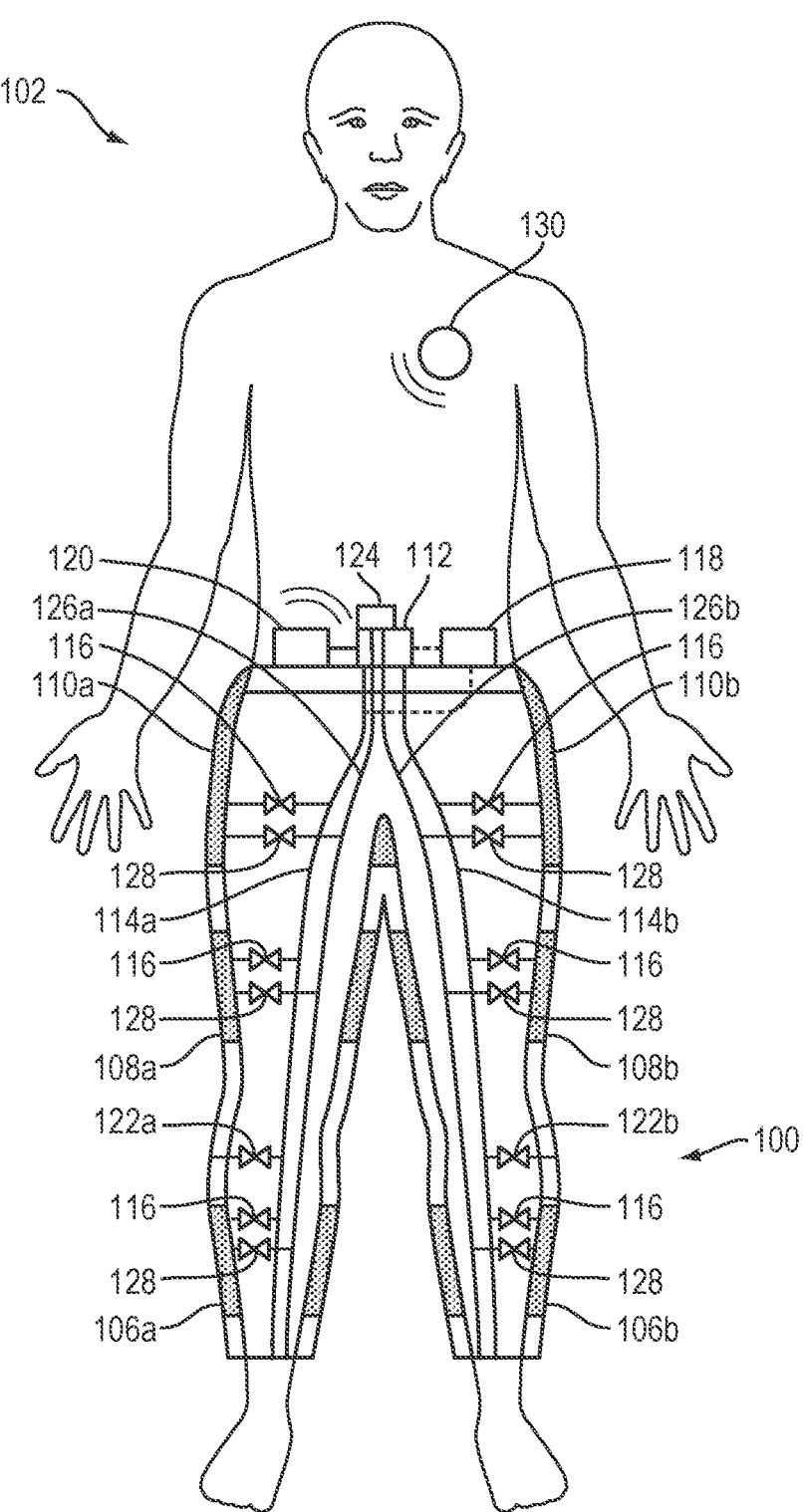
FIG. 4 is a schematic illustration of an ECP treatment device including a vacuum source, according to various embodiments.

In other embodiments, as shown for example in FIG. 4, the treatment device 100 can include a vacuum source 124 connected to vacuum trunk lines or manifolds 126a, 126b, each of which is dedicated to a leg of the user 102. The vacuum manifolds 126a, 126b can be connected to each of the inflatable cuffs via deflation valves 128. In such embodiments, the cuffs can be deflated by activating the vacuum source 124, closing inflation valves 116 and selectively opening particular deflation valves 128, depending on the cuff to be deflated. In still other embodiments, as shown for example in FIG. 5, each inflatable cuff can include a deflation valve 128 vented directly to ambient, as opposed to the vacuum source 124. In various embodiments, venting the vacuum source 124 to ambient can occur simultaneously or sequentially in any beneficial order.

In various embodiments, the compressor 112, storage tank 118, and valves 116, 128 are all controlled by a controller 120. The controller 120 can be connected to these components by wired and/or wireless connections. In general, the controller 120 can control activation of the compressor 112, opening and closing of the storage tank 118, and opening and closing of particular valves 116, 128 such that particular pulse sequences are applied to the body of user 102 in a beneficial manner. For purposes of illustration only, and without limiting this disclosure, the following is an example of how the controller 120 can operate to apply a particular pressure pulse sequence. In one embodiment, the controller 120 can activate the compressor 112 such that a pressurized gas fills manifolds 114a, 114b. Assuming that all valves are initially closed, the controller 120 can initially open the valves 116 associated with inflatable cuffs 106a, 106b disposed about the user's calve region, such that the cuffs 106a, 106b inflate and apply a pressure to the user 102. Without reducing the pressure applied by the previously-inflated cuffs 106a, 106b, the controller 120 can then open the valves 116 associated with the inflatable cuffs 108a, 108b disposed about the user's lower thigh region, such that the cuffs 108a, 108b inflate and apply a pressure to the user 102. Without reducing the pressure applied by any of the previously-inflated cuffs 106a, 106b, 108a, 108b, the controller 120 can then open the valves 116 associated with the inflatable cuffs 110a, 110b disposed about the user's upper thigh/buttock region, such that the cuffs 110a, 110b inflate and apply a pressure to the user 102. After all the cuffs 106a, 106b, 108a, 108b, 110a, 110b are inflated, the controller can open all of the deflation valves 128 such that all of the cuffs 106a, 106b, 108a, 108b, 110a, 110b deflate substantially simultaneously. The foregoing is meant to illustrate how the controller can control various system components to apply a particular pressure pulse train to the user 102. The components can be controlled differently and in different orders to apply pressure pulses of varying characteristics, some of which will be described in more detail below.

In various embodiments, the treatment device 100 includes a monitor 130 adapted to sense each heartbeat of the user 102. In some instances, the monitor 130 is an ECG device affixed in the chest region of the user 102, that generates electrical signals reflective of the depolarization corresponding to cardiac contraction and repolarization corresponding to cardiac relaxation. In other instances, the monitor 130 is an implantable device, such as a pacemaker or an ICD. Many other types of heartbeat monitors 130 are also contemplated, including those not affixed to the chest region of the user 102, such as pulse sensors applied to a finger tip. The monitor 130 can communicate heartbeat data to the controller 120 via a wired and/or wireless connection.

Figure 5:
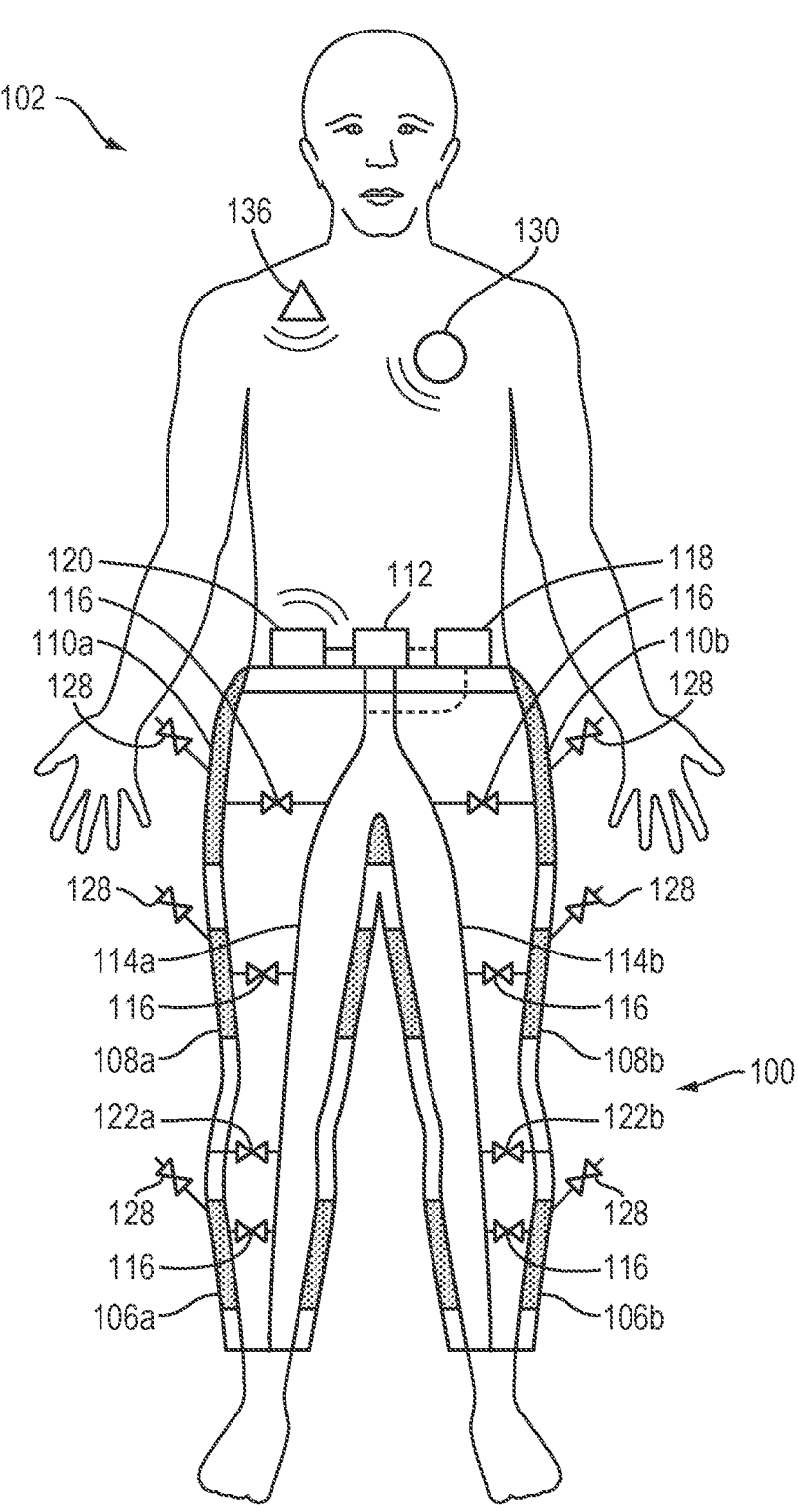
FIG. 5 is a schematic illustration of an ECP treatment device having deflation valves venting to the ambient, according to various embodiments.

In embodiments in which the treatment device 100 is a wearable garment, the compressor 112, storage tank 118, vacuum source 124, controller 120, and in some cases the monitor 130 can all be incorporated as part of the garment, so as to preserve the user's full ambulatory function. For example, as shown in FIGS. 3-5, these components can be located on a belt wrapped around the user's waist. The components can be located in many other locations, as well, e.g., on suspenders, on a headband, on an armband, etc. With recent advances in flexible electronics, certain components can be integrated into the body-conforming portions of the garment itself. In other embodiments, the components can be carried by a user in a backpack, satchel, and/or fanny pack. In other embodiments, one or more of the components can be placed in a case or on a cart with wheels.

In various embodiments, the controller 130 can control the timing and/or configuration of pulse sequence delivery based on heartbeat data received from the monitor 130. For example, as with conventional ECP devices, the controller 120 can sequentially inflate all three sets of inflatable cuffs 106a, 106b, 108a, 108b, 110a, 110b (as described above) during the diastole stage of the cardiac cycle and simultaneously deflate all three sets of inflatable cuffs 106a, 106b, 108a, 108b, 110a, 110b during the systole stage.

In addition, the treatment device 100 can apply different and/or more complex pulse sequences beyond those contemplated by conventional devices and techniques. In general, in addition to a single pulse per heartbeat, the controller 120 can apply any pulse sequence that may be beneficial for the user. For example, the controller 120 can control the compressor 112 (or in some cases storage tank 118) and valves 116, 128 to perform more than one pulse sequence (e.g., 2, 3, or more pulses) during the diastole stage. Examples of such pulse sequences are graphically depicted in the charts shown in FIGS. 6A and 6B.

Figure 6A:
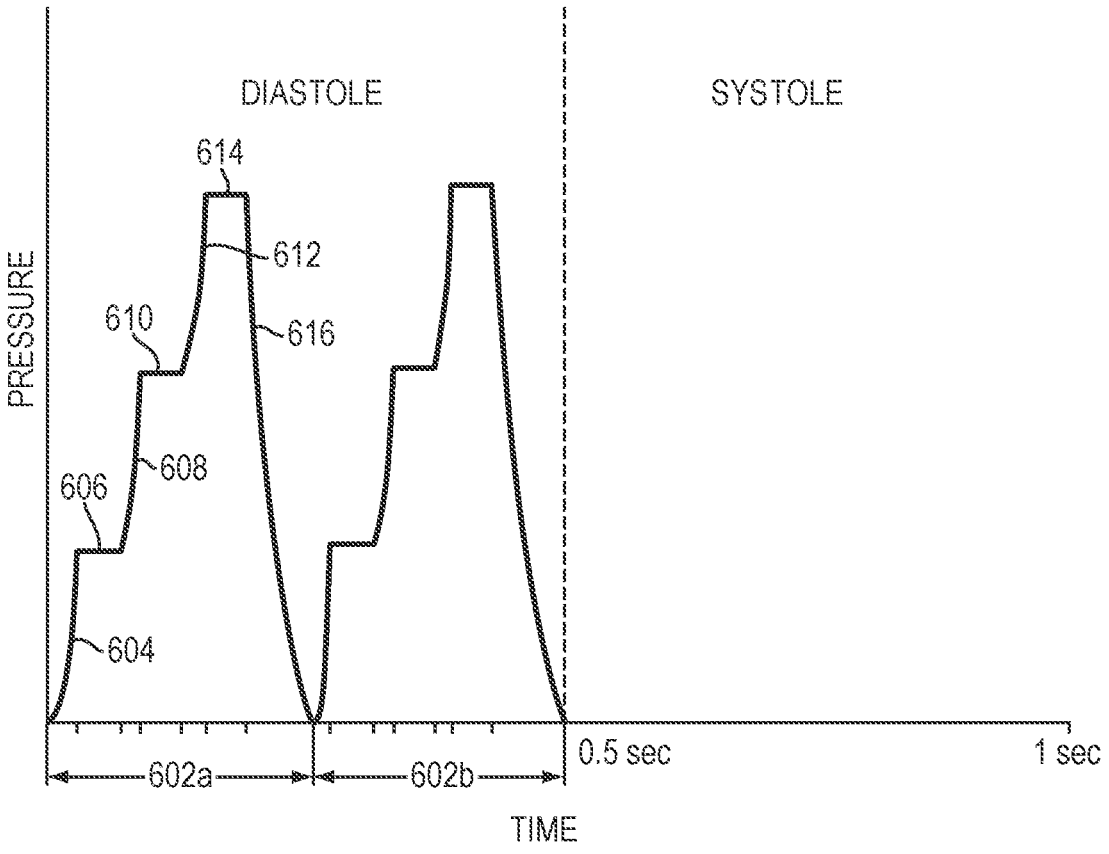
FIGS. 6A-B are charts showing pulse sequences that can be applied by an ECP treatment device in various embodiments.

FIG. 6A is a graph of pressure vs. time for 1 second, which is the length of a full cardiac cycle for a user with a heart rate of 60 bpm. For simplicity, the graph depicts the first half of the cardiac cycle (0.5 seconds) as the diastole stage and the second half (0.5 seconds) as the systole stage. As shown, this pulse sequence can include two sequential pulses 602a, 602b during the occurrence of a single diastole stage. Describing the first pulse 602a in more detail: (i) during time period 604, pressurized gas flows into the calf region inflatable cuffs 106a, 106b until they reach their fully inflated state at time period 606, at which time only the calf region inflatable cuffs 106a, 106b are applying pressure to the user; (ii) during time period 608, pressurized gas flows into the lower thigh region inflatable cuffs 108a, 108 until they reach their fully inflated state at time period 610, at which time both the calf region and lower thigh region inflatable cuffs 106a, 106b, 108a, and 108b are applying pressure to the user 102; (iii) during time period 612, pressurized gas is inserted into the upper thigh region inflatable cuffs 110a, 110b until they reach their fully inflated state at time period 614, at which time all of the inflatable cuffs 106a, 106b, 108a, 108b, 110a, 110b are applying pressure to the user 102; (iv) during time period 616 all three sets of inflatable cuffs are simultaneously deflated. As depicted, the pressure is shown to be sequentially increasing as additional cuffs are pressurized, to convey this process; however, the pressure in each cuff may be substantially the same as the one previously pressurized. Once the cuffs are deflated, the entire process is repeated before the end of the diastole stage, such that two full pressure pulses are applied during the diastole stage. Before the systole stage begins, all of the inflatable cuffs are deflated so that the blood vessels are unloaded when the heart contracts and pumps blood back into the limb. In some embodiments, the pulse sequence shown in FIG. 6A can be used if the user's heart rate is in a range from 50 bpm to 80 bpm.

Figure 6B:
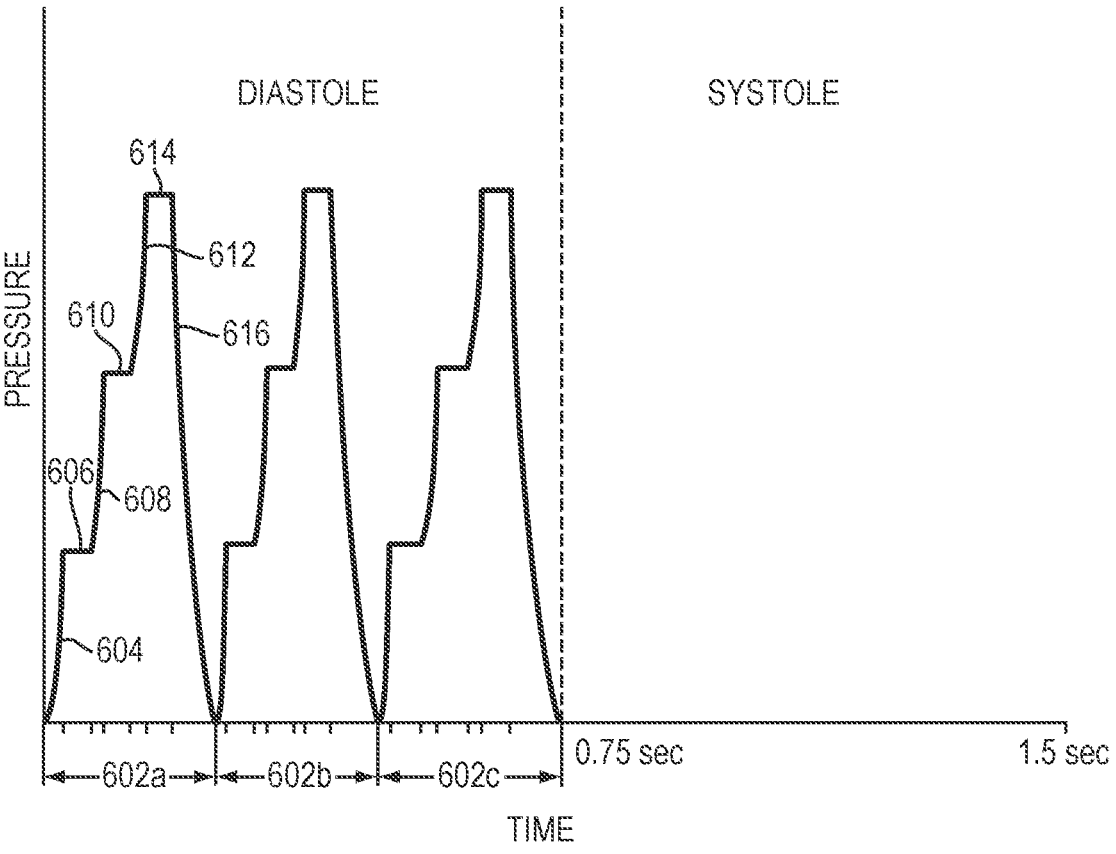

FIG. 6B is a graph of pressure vs. time for 1.5 seconds, which is the length of a full cardiac cycle for a user with a heart rate of 40 bpm. For simplicity, the graph depicts the first half of the cardiac cycle (0.75 seconds) as the diastole stage and the second half (0.75 seconds) as the systole stage. As shown, the pulse sequence can include three pulses 602a, 602b, 602c during the occurrence of a single diastolic stage. Each pulse 602a, 602b, 602c includes the same three stages as pulse 602*a* described in FIG. 6A above, but in FIG. 6B the pulse occurs three times during a single diastolic stage, instead of two times. Before the systole stage begins, all of the inflatable cuffs are deflated so that the blood vessels are unloaded when the heart contracts and pumps blood back into the limb. In some embodiments, the pulse sequence shown in FIG. 6B can be used if the user's heart rate is in a range from 30 bpm to 50 bpm. Other thresholds are contemplated including up to 10 bpm, 20 bpm, 30 bpm, 40 bpm, 50 bpm, 60 bpm, 70 bpm, 80 bpm, 90 bpm, 100 bpm and higher values and all ranges between any such recited values, as well as using any of these values as a minimum (e.g., at least 50 bpm).

In various embodiments, the sequential/simultaneous nature of the inflation/deflation of the cuffs for application of a pressure pulse can be different from that shown in FIGS. 6A and 6B. For example, all three sets of inflatable cuffs can be inflated simultaneously, rather than the sequential inflation described above. In some cases, all three sets of inflatable cuffs can be deflated sequentially (e.g., 110*a*, 110*b* first, 108*a*, 108*b* second, and 106*a*, 106*b* last), rather than the simultaneous deflation described above. In still other embodiments, any combination of cuffs can be grouped together for sequential or simultaneous inflation and/or deflation, as may be desirable for certain types of treatment. For example, cuffs 106*a*, 106*b* and 108*a*, 108*b* can be inflated simultaneously with cuffs 110*a*, 110*b* being inflated sequentially afterwards. Similarly, cuffs 110*a*, 110*b* and 108*a*, 108*b* can be deflated simultaneously with cuffs 106*a*, 106*b* being deflated sequentially afterwards.

As mentioned, the controller 120 is capable of applying many different pulse sequences beyond a single pulse per heartbeat and even beyond those shown in FIGS. 6A-B. As another example, the controller 120 can apply variable pulse sequences for a user exhibiting an irregular heartbeat. In some cases, the controller 120 can receive data from the monitor 130 indicating that the user's heartbeat is irregular. In general, when the user 102 exhibits an irregular heartbeat, the controller 120 can apply any suitable pulse sequences. For example, in some cases, the pulse sequence can include suspending application of any pulses until the heartbeat regularizes. In other cases, the pulse sequence can include stopping pulses for a predetermined amount of time (e.g., up to 1 second, up to 2 seconds, up to 3 seconds, up to 5 seconds, up to 10 seconds, up to 20 seconds, up to 30 seconds, up to 1 minute, etc.) and/or a predetermined number of cardiac cycles (e.g., 1, 2, 3, 5, 10, 20, 50, 100, etc.) and then resuming application of pulse sequences (e.g., any of the sequences described above), regardless of whether the heartbeat has regularized or not. Additional and/or refined pulse sequences can be used based on experimental results obtained using an animal model in a laboratory equipped with high fidelity blood flow instruments. The experiments can include placing the blood flow instruments inside the animal and observing the hemodynamic response of the animal in response to various pulse sequences. In some cases, the results of such experiments can be recorded using artificial intelligence computer technology and analyzed using software algorithms. The results can be used to design future treatment algorithms by customizing inflation and deflation pressure for particular users based on clinical results.

As mentioned, conventional ECP treatment devices are primarily used for the treatment of refractory angina. The pulse sequences and treatment techniques described above can be used to treat a wide array of other conditions.

In general, there are three levels of cardiovascular preventative care: primary care, secondary care, and tertiary care. Primary care involves reducing exposure to well-known coronary artery disease risk factors such as hypertension, hypercholesterolemia, diabetes, and smoking; secondary care involves minimizing the progression of disease after it has occurred; and tertiary care involves softening the impact of disease by improving long term function and quality of life. The ECP treatment techniques described herein can be used to provide all three types of cardiovascular care.

For primary cardiovascular care, the techniques can be used for the treatment of diabetes (e.g., type II mellitus). Studies have shown that 36 sessions of 1 hour daily conventional ECP treatment can significantly reduce advanced glycation end products, glycosylated hemoglobin (HbA1c) and proinflammatory cytokines concentrations at 3 months and 6 months post-treatment. One cause of the successful treatment is improved endothelial function in releasing higher level NO to mediate glucose uptake in the skeletal muscle.

For secondary cardiovascular care, as already discussed, the ECP treatments described herein can be effective in treating heart failure and patients with conditions causing refractory angina. A recent study showed that in a group of 1015 refractory angina patients, 55.2 percent were hospitalized, with an average of 1.7 hospitalizations/patient, during the 6 months before undergoing conventional ECP treatment. In the 6 months following conventional ECP treatment (35 hourly sessions), only 24.4 percent of the patients were hospitalized, with an average of 1.4 hospitalizations/patient. The study also found that in a group of heart failure patients, hospitalization was reduced by 6.3 percent 90 days following conventional ECP treatment.

For tertiary cardiovascular care, the ECP treatments described herein can improve functional capacity and reduce suffering of patients after they have experienced a cardiovascular event (e.g., a heart attack). In some instances, there are synergies between ECP therapy and cardiac rehabilitation, as the physiological features between the two have similarities, e.g., both work to improve systemic circulation, reduce arterial stiffness, and improve endothelial function. In some instances, the ECP treatments described herein can help patients to overcome residual effects (e.g., angina or other) resulting from the event. In some instances, the ECP treatment can be a viable substitute for exercise until the patient is healthy enough to exercise on their own. The treatment can help patients to overcome their fear of exercise and serve as a bridge to prevent patient regression from lack of cardiac rehabilitation (e.g., exercise).

Continuing with the concept of the synergies between ECP therapy and exercise, in various embodiments the ECP treatments described herein can be used by relatively healthy individuals who wish to experience the cardiovascular benefits of exercise, without performing traditional exercise actions such as running. The desires to avoid traditional exercise are numerous, including a desire to avoid impact trauma on joints, a desire to avoid soreness, a desire to save time, and/or a lack of motivation or ability, to name a few. The ECP treatments described herein can be used by individuals within their homes or workplaces and can offer many of the benefits of exercise without the disadvantages described above. In some embodiments, the ECP treatments can be configured to generate a predetermined desired heart rate for the user, which in some instances can be set by the user (e.g., using a user interface electronically connected to the controller). In general, the predetermined heart rate can be any desirable heart rate, for example, approximately 80 percent of 220 minus the user's age.

In other embodiments, instead of being used as a substitute for exercise, the ECP treatments described herein can be used as a supplement to exercise. For example, individuals that engage in active exercise routines can undergo the treatment as a supplement when they are unable to exercise (e.g., at the office, on a bus or train, etc.) As another examples, serious athletes such as professional athletes, marathon runners, etc., can use the treatment to avoid over-exercising and harming their bodies with conditions such as shin splits, runner's knee, etc. In still other embodiments, the treatments described herein can be used in conjunction with exercise routines. For example, a user 102 can wear the treatment device 100 while engaging in an exercise (e.g., running on a treadmill). In some cases, this can result in an improved exercise experience and/or result.

In various embodiments, the ECP treatments described herein can be used to treat conditions other than cardiac conditions. For example, the ECP treatments can be used for the treatment of dementia (e.g., Alzheimer's disease). There is evidence suggesting that the pathological conditions associated with mild cognitive impairment (MCI) and dementia associated with aging come from (i) cerebrovascular dysfunction, which decreases bioavailability of NO and increases exposure to inflammatory cytokines and oxLDL and (ii) ED in the blood brain barrier, which can lead to leakage of damaging or toxin materials into the brain. The ECP treatments described herein can have the pathophysiological benefits of improving bioavailability of NO and reducing exposure to toxins and the effects of ED. Because the system is noninvasive, the ECP treatments can be beneficial in treating patients with early-stage forgetfulness. The treatments can act as preventative care to improve function of the blood brain barrier and prevent the disease from progressing to full-blown dementia.

In various embodiments, the ECP treatment techniques described herein can be used to treat patients with progressive renal disease, e.g., from stage 3 to 5 (stage 5 typically requiring dialysis or transplant). In some instances, the treatment techniques can also be used to treat patients with chronic kidney disease (CKD). There is clinical evidence showing the safety and effectiveness of conventional ECP treatment in improving kidney function in CKD. In various instances, the treatment can stop progression of the disease and/or prevent CKD stage 3 or stage 4 patients from reaching stage 5 and needing dialysis. The benefits of such treatment are potentially quite large. In the United States, there are approximately 26 million people with CKD; approximately 8 million with stages 3-4 and approximately 111,000 per year with stage 5. The cost of dialysis per year is approximately $24.3 billion. Patients with stage 5 kidney failure suffer from dramatically reduced quality of life and the primary means for positive resolution is transplantation, which can be extremely expensive and is accompanied by continuing chronic and intensive medical management for the remainder of the patient's life.

In various embodiments, the ECP treatment techniques described herein can be used to treat patients with Cardiac Syndrome X (CSX, also known as microvascular angina or coronary microvascular dysfunction). CSX afflicts approximately 20 percent of patients exhibiting chest pain. Many current treatment techniques for CSX have been ineffective. Patients sometimes undergo coronary angiography because the chest pain is thought to be due to obstructive coronary artery disease (CAD); however, no significant epicardial arterial obstruction is found. Pathogenesis often includes ED, smooth muscle cell dysfunction, and vascular remodeling. In the United States, approximately 3 to 4 million patients have this disease, with its associated poor quality of life and physiological distress. In some instances, the ECP treatments described herein can offer relief and effective treatment.

In various embodiments, the ECP treatment techniques described herein can be used to treat patients with acute myocardial infarction (AMI) (e.g., a heart attack), cardiogenic shock, and/or septic shock. As mentioned, conventional ECP treatments have been used as preventative care in an attempt to prevent these events from occurring and as follow-up care after these events. The ECP treatment techniques described herein can be taken a step further and be applied while these events are occurring. For example, while a patient is experiencing a heart attack, the ECP treatment can be applied in conjunction with manual or automated chest compression during cardiopulmonary resuscitation. In some cases, the ECP treatment can be the primary treatment. In other cases, the ECP treatment can be a supplement to primary care (e.g., applied by a defibrillator), for example, to alleviate pain, reduce side effects, etc.

The use of ECP treatment during these events can have a significant impact. Certain statistics of individuals experiencing myocardial infarction and cardiogenic shock, which are heart-related events, are given above. As for septic shock, more than 18 million cases of severe sepsis occur worldwide each year, killing approximately 1400 people daily. In general, septic shock occurs when infection disrupts blood flow to the brain and/or kidneys, causing blood pressure to drop, which can lead to respiratory, heart, and/or organ failure, and in some cases death.

In various embodiments, the ECP treatment device used during acute myocardial infarction (AMI), cardiogenic shock, and/or septic shock can take any of the forms described above or other forms. As one example, the ECP treatment device can be included in a kit adapted to be used by EMT professions, in some cases, in an ambulance. The kit can include attachable inflatable cuffs and control electronics, as described above.

In some embodiments, an ECP treatment device performing cardiac resuscitation can receive signals from the heartbeat monitor 130, as described above, for example, in situations in which the user still has a heartbeat (even if reduced or irregular). However, in other embodiments, a user requiring cardiac resuscitation may have no heartbeat, or it may be undesirable to base pressure pulse treatment on such a heartbeat profile. As such, in other embodiments, an ECP treatment device can be adapted to apply pressure pulses based on applied chest compressions. The chest compressions can be applied by a defibrillator device (e.g., an automatic external defibrillator (AED)), a resuscitation machine, a human applying CPR, or any other technique. In such embodiments, the controller 120 controls the inflatable cuffs to apply pressure pulse sequences based on the occurrence of chest compressions (e.g., one pulse per compression, two pulse sequences per compression, three pulse sequences per compression, etc.), simultaneous with or out-of-phase with chest compressions. In such embodiments, the treatment device 100 can include a chest compression monitor 136 (see FIGS. 5 and 7) in addition to, or as an alternative to, the heartbeat monitor 130. The chest compression monitor 136 can be adapted to monitor when the user's chest is compressed. In other instances, the controller 120 is adapted to communicate with an external chest compression monitor, e.g., those included in standard chest compressions technologies (e.g., defibrillators).

Figure 7:
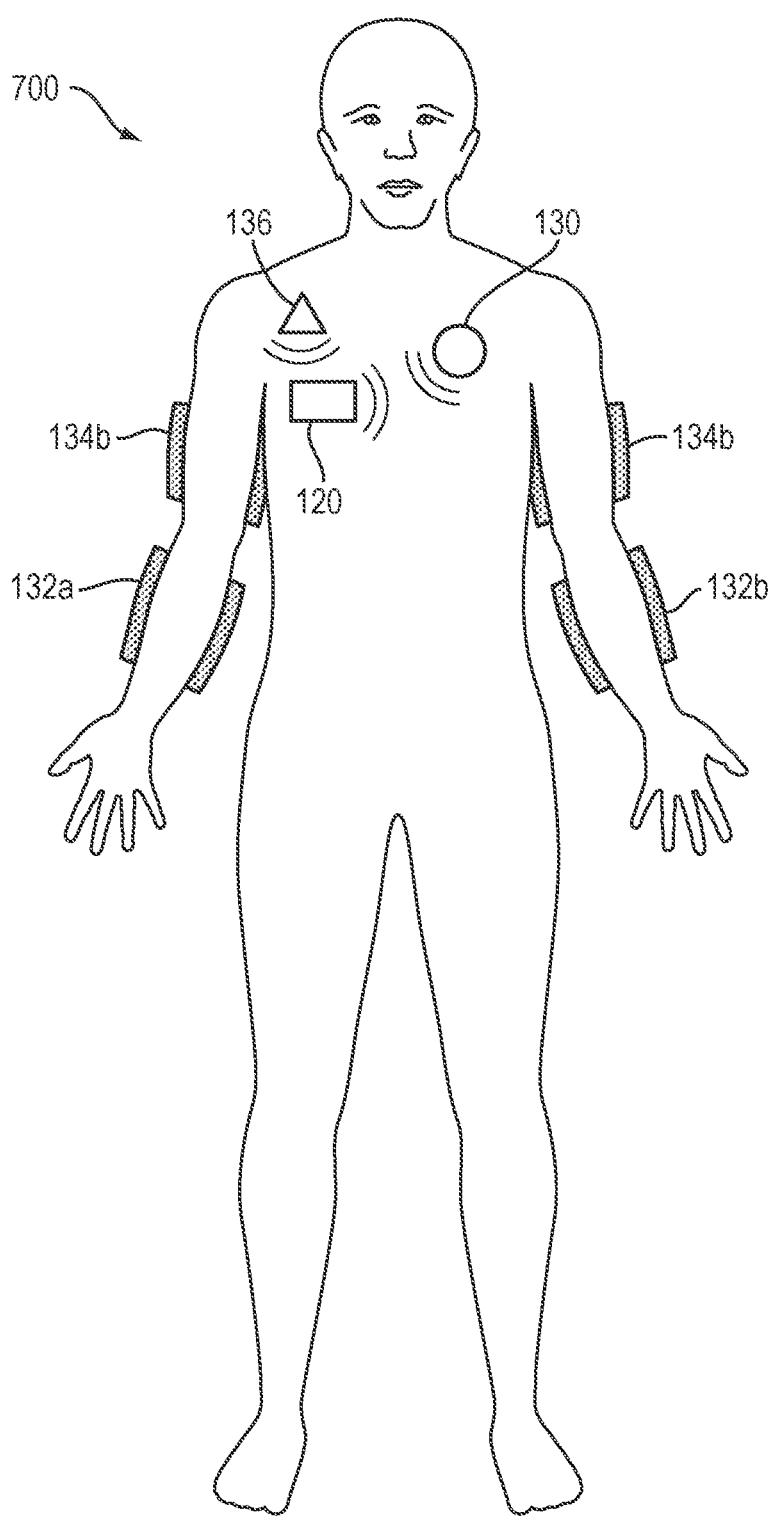
FIG. 7 is a schematic illustration of an ECP treatment device applied to a user's arms, according to various embodiments.

In various embodiments, as shown for example in FIG. 7, a treatment device 700 can include inflatable cuffs 134a, 134b wrapped around a user's upper arm (e.g., bicep) and, in some cases, inflatable cuffs 132a, 132b wrapped around a user's lower arm (e.g., forearm). Although this disclosure will generally describe the treatment device 700 as including two sets of inflatable cuffs, in various embodiments, the treatment device 700 can include less cuffs (e.g., 1 cuff) or more cuffs (e.g., 3, 4, or 5 cuffs) disposed about a user's arms. The treatment device 700 can function similarly to those described above, but instead of applying pressure pulses to a user's legs it applies pressure pulses to the user's arms. Because the arms are located closer to a user's heart and brain, in some instances, application of pressure pulses to the arms can result in improved circulation in those areas (or other areas). Improved circulation (e.g., caused by inflatable cuffs on the upper or lower extremities) can be used to treat many neurological conditions, e.g., strokes, insomnia, Alzheimer's disease, Parkinson's disease, etc.

In general, any concept described above with relation to treatment device 100 applied to the user's legs can apply to treatment device 700 applied to the user's arms. As shown in FIG. 7, the treatment device 700 can include a controller 120 adapted to control inflation and deflation of inflatable cuffs 132a, 132b, 134a, 134b in the same manner as described above for inflatable cuffs 106a, 106b, 108a, 108b, 110a, 110c. In some cases, the controller 120 can control inflation/deflation based on data received from a heartbeat monitor 130. In other instances, the controller 120 can control inflation/deflation based on data received from a chest compression monitor 136.

In various embodiments, the treatment device 700 can be used alone without any inflatable cuffs disposed about the user's legs. In other embodiments, the treatment device 700 can be used in conjunction with the treatment device 100, such that the user 102 receives pressure pulses to both the arms and the legs. In such instances, the treatment device 700 and the treatment device 100 can apply pressure pulses in unison or out-of-phase from each other. Similarly, the treatment device 700 and the treatment device 100 can apply the same pressure pulse sequence or different pressure pulse sequences.

Each numerical value presented herein is contemplated to represent a minimum value or a maximum value in a range for a corresponding parameter. Accordingly, when added to the claims, the numerical value provides express support for claiming the range, which may lie above or below the numerical value, in accordance with the teachings herein. Absent inclusion in the claims, each numerical value presented herein is not to be considered limiting in any regard.

The terms and expressions employed herein are used as terms and expressions of description and not of limitation and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. The structural features and functions of the various embodiments may be arranged in various combinations and permutations, and all are considered to be within the scope of the disclosed invention. Unless otherwise necessitated, recited steps in the various methods may be performed in any order and certain steps may be performed substantially simultaneously. Accordingly, the described embodiments are to be considered in all respects as only illustrative and not restrictive. Furthermore, the configurations described herein are intended as illustrative and in no way limiting. Similarly, although physical explanations have been provided for explanatory purposes, there is no intent to be bound by any particular theory or mechanism, or to limit the claims in accordance therewith.

What is claimed is:

1. A counterpulsation system comprising:
   a monitor adapted to sense a heartbeat and a heart rate of a user;
   a pulsation unit adapted to apply pressure pulses to at least a lower body of the user; and
   a controller adapted to receive sensed heartbeats from the monitor and to control the pulsation unit to (i) apply three pulses between successive heartbeats when the heart rate of the user is in a range from 30 bpm to 50 bpm and (ii) apply two pulses between successive heartbeats when the heart rate of the user is in a range from 50 bpm to 80 bpm.

2. The counterpulsation system of claim 1, wherein the pulsation unit is externally disposed about at least one of a buttock region, a thigh region, a hip region, and a leg region of the user.

3. The counterpulsation system of claim 1, wherein the pulsation unit comprises an inflatable sleeve.

4. The counterpulsation system of claim 1, wherein at least one of the monitor and the pulsation unit communicates wirelessly with the controller.

5. The counterpulsation system of claim 4, wherein the counterpulsation system comprises a wearable garment.

6. The counterpulsation system of claim 1, wherein the counterpulsation system permits the user to be ambulatory.

7. A method for applying counterpulsations to a user, the method comprising the steps of:
   sensing heartbeats of the user;
   sensing a heart rate of the user; and
   applying (i) three pulses between successive heartbeats when the heart rate of the user is in a range from 30 bpm to 50 bpm and (ii) two pulses between successive heartbeats when the heart rate of the user is in a range from 50 bpm to 80 bpm.

8. The method of claim 7, wherein the applying step is performed by a pulsation unit externally disposed about at least one of a buttock region, a thigh region, a hip region, and a leg region of the user.

9. The method of claim 7, wherein both the measuring and applying steps occur while the user is ambulatory.

10. The method of claim 7, further comprising the step of: first determining that the user requires cardiac resuscitation.

11. The method of claim 7, further comprising the step of: first determining that the user has a cognitive impairment.

12. The counterpulsation system of claim 1, wherein the counterpulsation system is adapted to perform a therapy treatment.

13. The counterpulsation system of claim 1, wherein the counterpulsation system is adapted to perform cardiac resuscitation on the user.

14. The counterpulsation system of claim 1, wherein the counterpulsation system is adapted to treat a cognitive impairment of the user.

* * * * *